United States Patent [19]

Kremer et al.

[11] Patent Number: 4,598,714
[45] Date of Patent: * Jul. 8, 1986

[54] APPARATUS FOR MEASURING THE THICKNESS OF CORNEAS

[75] Inventors: Frederic B. Kremer, Bala Cynwyd; Edward R. O'Brien, Wayne, both of Pa.

[73] Assignee: Accutome, Inc., Frazer, Pa.

[*] Notice: The portion of the term of this patent subsequent to Oct. 15, 2002 has been disclaimed.

[21] Appl. No.: 468,289

[22] Filed: Feb. 22, 1983

[51] Int. Cl.$^4$ .............................................. A61B 10/00
[52] U.S. Cl. ...................................... 128/660; 73/612
[58] Field of Search ................... 128/660, 29 A, 661, 128/303.14–303.16, 305, 305.5, 24 A, 745; 73/609–612, 615, 617

[56] References Cited

U.S. PATENT DOCUMENTS 3,371,660 3/1968 Carlin .................................... 128/660
3,827,287 8/1974 Boggs et al. ...................... 73/615 X
4,261,367 4/1981 Freese ................................. 128/660

OTHER PUBLICATIONS

Wells, P. N. T. "Ultrasonics in Clinical Diagnosis", Churchill Livingstone, N.Y. 1977, pp. 87–96.

Primary Examiner—Kyle L. Howell
Assistant Examiner—Francis J. Jaworski
Attorney, Agent, or Firm—Steele, Gould & Fried

[57] ABSTRACT

An apparatus is disclosed for measuring the thickness of the corneas. Corneal thickness is measured by first directing ultrasonic pulses towards the cornea and timing the interval between reflected pulses. The apparatus also includes a pulse stretcher for enlarging the width of the pulse representing the interval between pulses reflected from the inner and the outer surfaces of the cornea, so that the time between pulses can be accurately measured by a conventional, low-frequency electronic clock. The invention further comprises electronic gating means for rejecting spurious pulses.

6 Claims, 14 Drawing Figures

APPARATUS FOR MEASURING THE THICKNESS OF CORNEAS

DESCRIPTION

The present invention comprises an apparatus for measuring the thickness of corneas. Surgical treatment of the eye in numerous instances requires a partial thickness incision of the cornea. Examples where such incisions are required, include radial keratotomy, initially relaxing incisions, wedge resections, lamellar keratoplasty, tumor excisions, etc. The apparatus disclosed herein improves the safety and accuracy with which these procedures can be executed.

Radial keratotomies involve the reshaping of the cornea to reduce refractive error. In 1974, Fyodorov developed a technique in Moscow for making partial thickness radial corneal incisions for the reduction of myopia (nearsightedness). Since that time, the procedure has been performed on over 1500 persons in the Soviet Union. A review of the risks and benefits of this procedure is expected to be published in the Annals of Ophthalmology. It is anticipated that the possibility of corneal perforation will be exposed as a major problem inherent in the procedure. If such perforation occurs there is risk of infection and ensuing visual loss. One purpose of the present invention is to reduce greatly this risk.

In the prior art, for example, U.S. Pat. No. 4,154,114, ultrasonic pulses have been employed to determine distances between points in the body. However, most instruments previously used to measure distances within the eye utilize an ultrasonic probe having a tip which touches the cornea in a manner which can introduce small but significant errors. These instruments use the probe tip echo to represent the anterior cornea surface. But in fact, the probe tip is seldom coincident with the surface of the cornea, and so the opportunity for an error is possible in the measurement.

Another problem in the use of ultrasonic techniques to measure corneal thickness is the fact that the cornea is thin. Pulses reflected from the anterior cornea surface (i.e. the outer surface) and the endothelium surface (i.e. the inner surface) are separated by such a short interval as to make it difficult to accurately measure the time interval between pulses using classical techniques. Although most ocular element distances are of order of 2–25 mm, the human cornea is only about 0.4–1.0 mm thick, so the time between echo pulses can be as short as 500 nanoseconds. In order to measure the distance between pulses, a clock frequency of approximately 80 MHz would be required instead of the typical 8 MHZ clock frequency used in present ocular element measurement systems.

The requirement of a high frequency clock introduces several technical problems. Standard transistor-transistor logic (TTL) elements can not be used in gating and counting circuits because the maximum operation frequency for TTL is 40 MHz before restrictions and problems set in. Secondly, emitter-coupled logic (ECL) could be used, but ECL is very susceptible to noise transients and the complexity of the circuit board layout is greatly increased.

One approach that has been suggested for solving the high clock frequency problem discussed above would be to average individual measurement cycles at a lower clock rate. With this method, instead of the counter being reset after each single real-time pulse measurement, the counter is allowed to count up for a predetermined number of pulse echo cycles (such as 100) and therefore, the clock frequency could be decreased. This approach presents at least two problems. First, the accuracy of the measurement is a function of the number of samples taken. Greater accuracy can sometimes be obtained with a larger sample, but at the expensve of more time. In certain approaches to corneal surgery, this extra time may not be available. Secondly, to use statistical averaging approach, it is mandatory that the clock frequency be totally independent of the circuit which generates the ultrasonic pulse signals. Due to the radio frequency (rf) energy which is emitted while generating these pulses, it is extremely difficult to prevent this energy from influencing the counter frequency, thereby degrading the statistical sampling.

SUMMARY OF THE INVENTION

The present invention solves the above-described problems by providing an apparatus with which: A pulse of energy, preferably an ultrasonic pulse, is directed towards the eye from a hand-held transducer, and reflected pulses are received. The ultrasonic transducer has a plastic water filled probe tip which transmits the ultrasonic pulses directly to the anterior corneal surface (ACS). The ACS therefore is the first echo pulse to be received. This pulse arms a gate which then expects to receive a reflected pulse from the posterior corneal surface. (PCS). To summarize if a reflected pulse from the anterior cornea surface is received within an anticipated time window, the apparatus then prepares to receive a pulse reflected from the posterior corneal (endothelial) surface (PCS), also within a reasonable time window. The time interval between the reflected pulses from the anterior corneal surface (ACS) and the posterior corneal surface (PCS) represents the thickness of the cornea.

The two reflected pulses, from the ACS and the PCS, are converted into a single gate pulse which begins with the ACS pulse and ends with the PCS pulse. This gate pulse is then stretched by a predetermined factor, such as 10, and its width is measured by counting the number of pulses emitted by an electronic clock during the time that the stretched gate pulse is present. The width is converted to a corresponding distance (based on the acoustic velocity of the cornea) and is displayed digitally.

After the corneal thickness has been accurately measured in the above manner, this measurement may be used to manually adjust a separate hand-held blade to the proper length.

It is therefore an object of the present invention to provide an improved method of performing corneal surgery which is both safe and accurate.

It is a further object of the present invention to provide an apparatus which measures the corneal thickness in a manner substantially free from errors due to spurious reflected pulses.

It is a further object of the present invention to provide a pulse stretcher which permits the measurement of corneal thickness using conventional techniques.

Other objects and advantages of the present invention will be apparent to those skilled in the art from a reading of the followiing detailed description of the invention, and appended claims, and by referring to the accompanying drawings wherein like reference characters refer to similar parts throughout and wherein:

DETAILED DESCRIPTION OF THE INVENTION

Before describing the present invention in detail, it is helpful to explain the particular problems which need to be solved in the performance of corneal surgery.

Figures 1, 2:
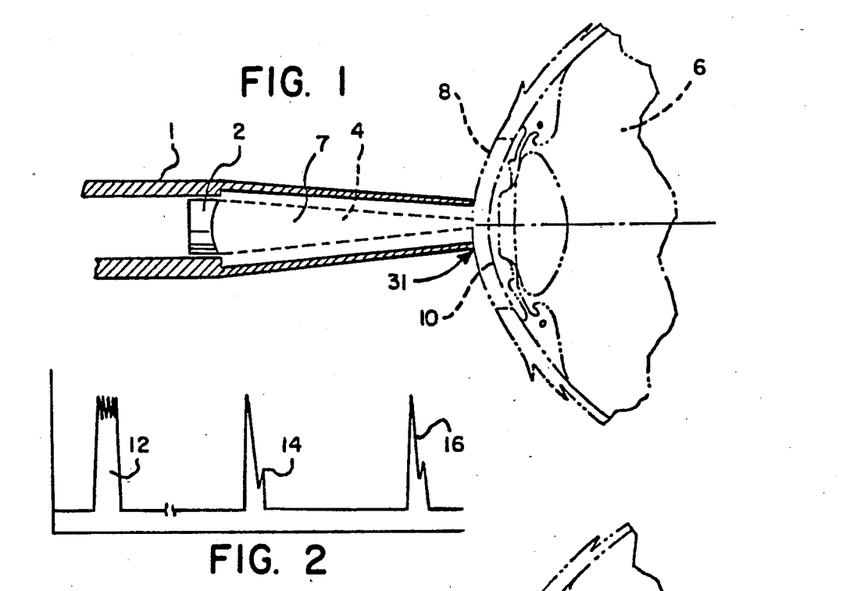
FIG. 1 is a cross-sectional view of the probe touching the surface of the eye in an idealized, hypothetical application, wherein the end of the probe corresponds precisely to the outer surface of the eye.
FIG. 2 is a diagram showing the relative amplitudes and shapes of the pulse directed towards the eye and the two reflected pulses in the idealized configuration of FIG. 1.
Figures 9, 10, 11:
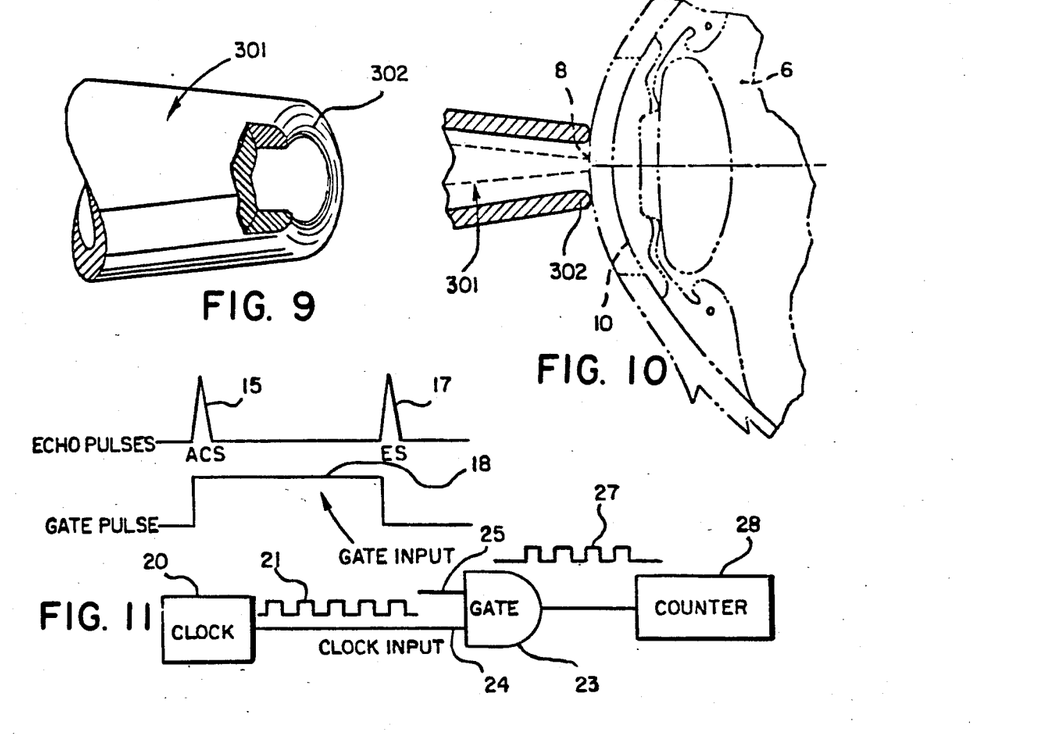
FIG. 9 is a fragmentary perspective view of the probe tip which is applied to the surface of the eye, partially broken away to expose interior construction details.
FIG. 10 is a cross-sectional view of the probe tip as applied to the cornea.
FIG. 11 is a block diagram indicating the conventional means by which reflected pulses are converted into a measurement of corneal thickness.

FIGS. 1, 2 and 11 illustrate the ideal configuration for measuring corneal thickness. In FIG. 1 the probe 1 contained a forward ultrasonic transducer 2 which emits ultrasonic waves, as indicated by the dashed lines 4, through a water medium 7, towards the eye 6. Preferably, the water medium 7 is water, which will remain within the interior cavity defined by the probe tip through surface tension. Ultrasonic pulses are reflected from the anterior corneal surface 8 (ACS) and from the posterior corneal surface 10 (PCS) (i.e. the inner surface) and are reconverted into electrical energy at the transducer 2. It should be noted that in the ideal configuration of FIG. 1, the end of probe 1 lies precisely along anterior cornea surface 8.

FIG. 2 shows the sequence of pulses resulting from the arrangement of FIG. 1. Pulse 12 represents the initial pulse (main bang) which is directed towards the eye; pulse 14 represents the first reflected pulse, i.e., the pulse from the anterior cornea surface; pulse 16 represents the reflection for the posterior cornea surface.

Figures 5, 6:
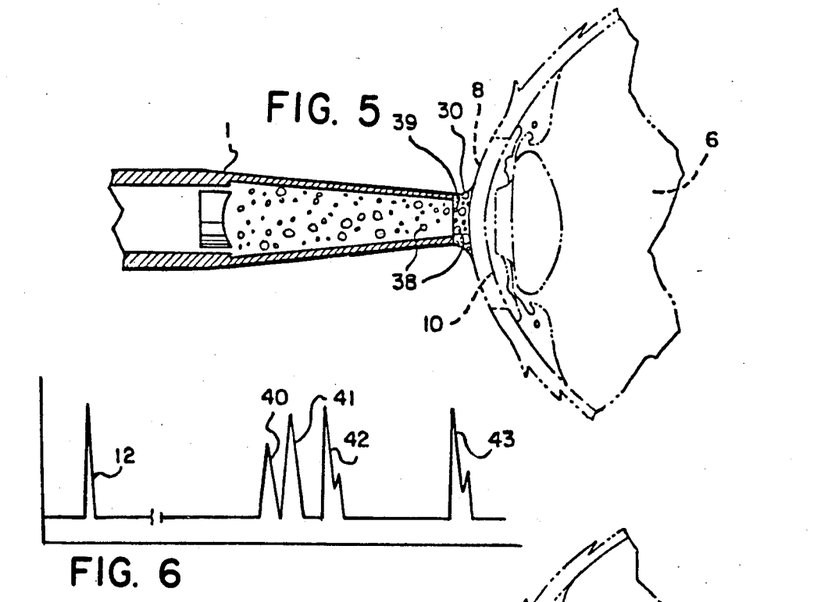
FIG. 5 is a side view of a probe applied to the eye wherein there are bubbles or foreign matter trapped in the liquid.
FIG. 6 is a diagram showing the amplitudes of the reflected pulses resulting from the configuration of FIG. 5.

There is a problem which can arise when the idealized configuration of FIGS. 1, 2 and 11 is put into practice. As illustrated in FIG. 5, bubbles 38 and/or foreign matter 39 may be trapped in the water 7 or liquid film 30 and may cause distortion in the received pulses. As shown in FIG. 6, intermediate peaks 40 and 41 may also be observed, these peaks being caused by reflections for the bubbles and foreign matter. The pulses 42 and 43 correspond to the pulses 14 and 16 of FIG. 2, respectively, but may be reduced in amplitude, due to the poor transition through the mixture (liquid, bubbles and/or foreign matter).

Figure 7:
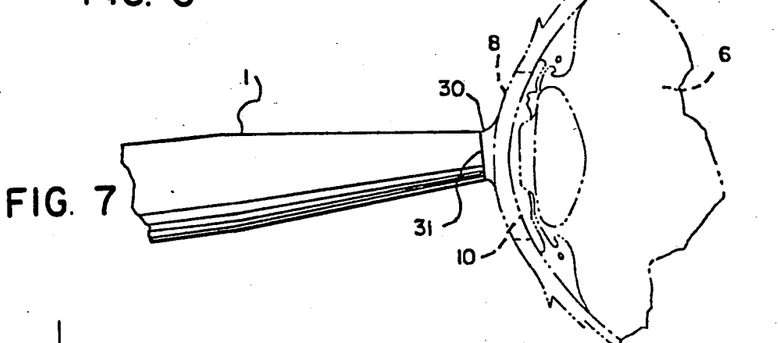
FIG. 7 is a side view of a probe touching the eye while the probe tip is slightly tilted, thereby introducing error.
Figure 8:
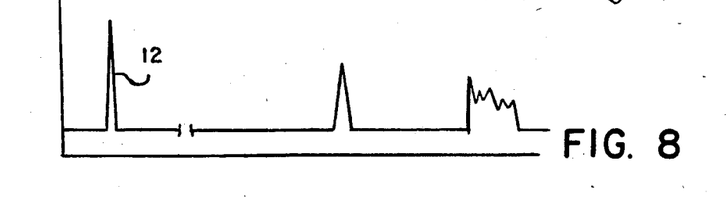
FIG. 8 is a diagram showing the relative amplitudes of the reflected pulses as observed in the configuration of FIG. 7.

An advantage inherent with the idealized configuration of FIG. 1 is illustrated in FIG. 7. The probe 1 is slightly tilted so that the cornea echo pulse would be greatly reduced in magnitude. The shape of such a reflected pulse is illustrated in FIG. 8. The pulse 46 and the pulse 47 represent reflections from the cornea. This reduction in pulse amplitude would not allow the necessary gates to be triggered, thus avoiding a non-perpendicular and erroneous reading from being taken.

Figures 3, 4:
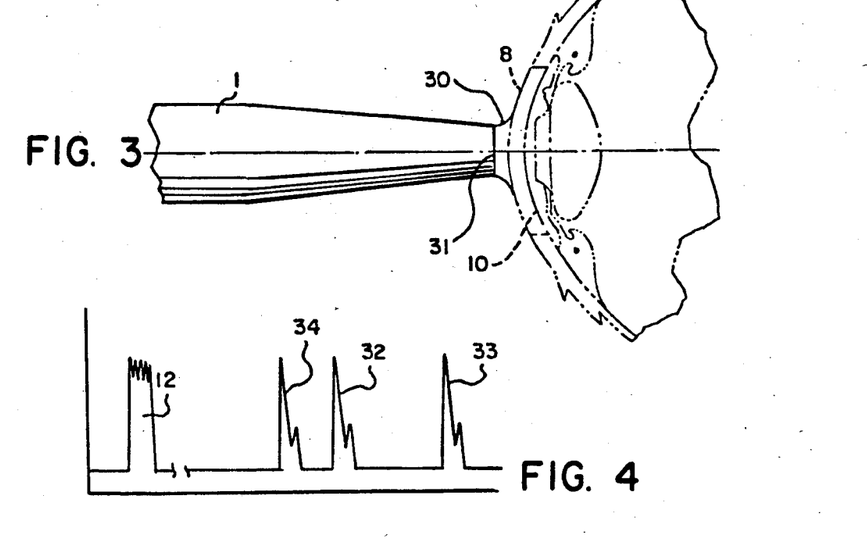
FIG. 3 is a elevational view of a modified ultrasonic probe applied to the eye, wherein there is a thin layer of liquid film between the probe tip and the cornea and wherein the probe is solid.
FIG. 4 is a diagram showing the relative amplitudes of the pulses reflected from the eye, in the configuration of FIG. 3.

Another advantage of the liquid filled probe tip is inherent in the design of FIG. 1. Should the tip of probe 1 not actually rest on the corneal surface 8, there may be a liquid film similar to the film 30 formed between the tip 31 of probe 1 and the cornea surface 8. Because the probe 1 is liquid filled, only pulses 32 and 33 as shown in FIG. 4 from the anterior cornea surface 8 and the posterior surface 10, will be generated. Spurious pulse 34 would not be generated. This spurious pulse would result, however, with the solid probe tip. See FIG. 3.

As best seen in FIGS. 9 and 10, in the preferred embodiment, the probe 301 is provided with a forward ring or tip 302 in position to contact the anterior cornea surface 8 in substantially circular overall contact to thereby discourage the generation of undefined cornea echo pulses 40 and 41 (FIG. 6) and to define a definite initial pulse 14 (FIG. 2) representing the anterior cornea surface 8.

FIG. 11 illustrates how the reflected pulses are converted into a usable numeral output. The pulses 15 and 17, which are schematically illustrated in FIG. 11, correspond to the pulses 14 and 16 of FIG. 2 and represent the anterior cornea surface and the posterior cornea surface as described above. Through appropriate circuitry (to be described below), these pulses are converted into a gate pulse 18, which begins with the anterior cornea surface pulse and ends with the posterior cornea surface pulse. A clock 20, which generates a constant string of pulses 21 of equal amplitude and spacing, is connected to AND gate 23 at the input line 24. The input line 25 is connected to the source of the gate pulse 18. When the gate pulse 18 begins, the AND gate 23 allows clock pulses to pass through the gate and the output of the gage 23 will be the pulses 27. These output pulses 27 are counted in the usual manner by the counter 28. The number of such pulses therefore represents the width of the gate pulse 18, which in turn represents the thickness of the cornea.

As indicated above, still another problem encountered in measurement of corneal thickness by ultrasonic techniques is caused by the extreme thinness of the cornea. The actual time between the pulses 15 and 17 in FIG. 11 would actually be only in the range of 0.4 to 1.2 microseconds. In order to determine accurately the length of the gate pulse 18, it is necessary to use a clock having pulses 21 with widths substantially shorter than that of the pulse 18. Therefore, in order to use the configuration of FIG. 11, it is necessary to provide a clock with a pulse frequency of 80 MHz, which is impractical for the reasons discussed earlier.

Figure 13:
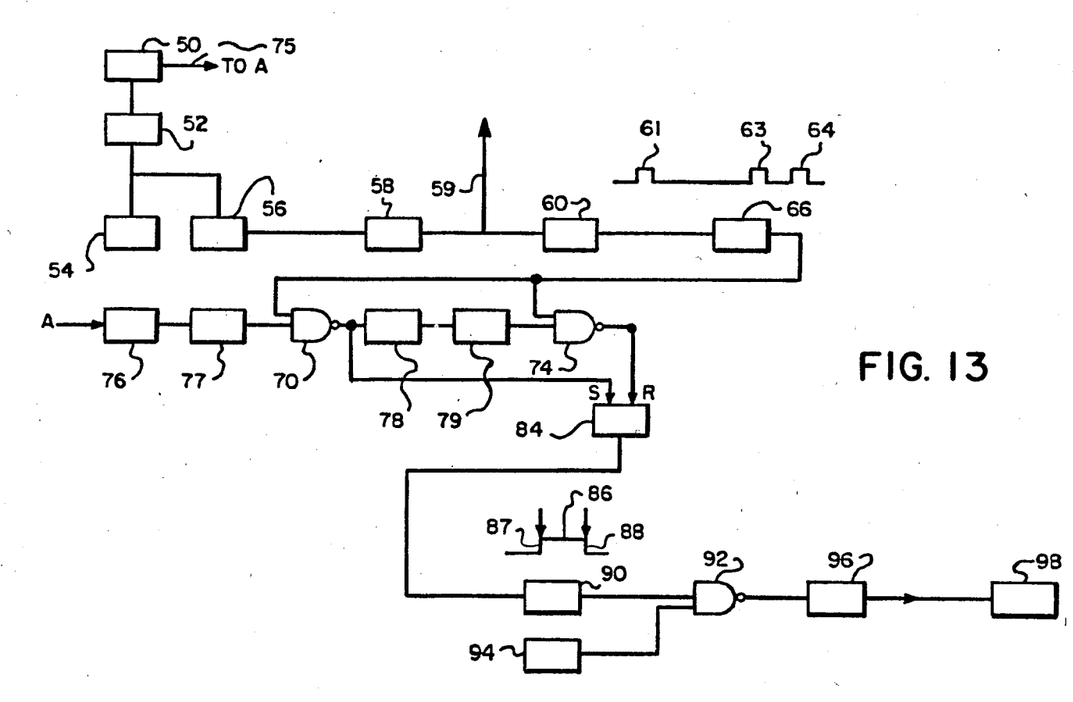
FIG. 13 is a block diagram of the preferred embodiment of the present invention.

A block diagram of an apparatus which solves the above problems is illustrated in FIG. 13. This apparatus is an ultrasonic pachometer, or "Corneometer". The "Corneometer" functions as follows: Pulses are generated by the clock 50, which preferably generates pulses having a frequency of 5 kHz. The clock pulses are used to excite an ultrasonic generator 52 which drives a transducer 54 which converts electrical pulses into ultrasonic energy in known manner. When the ultrasound beam from the transducer encounters a surface, or object, part of the energy is reflected back to the transducer. These reflected echo pulses are converted to electrical energy again by the transducer 54, and the echo pulses are fed into the amplifier 56 and to the absolute value rectifier 58. The line 59 may be connected to a cathode ray tube (not shown) if it is desired to display the echo pulses at this stage. The echo pulses are then fed through a comparator 60, which compares the echo pulse with a threshold value so as to distinguish the echo pulses from noise. The configuration of the detected pulses that would be expected is illustrated schematically as the pulses 61, 63 and 64. Pulse 61 represents the so-called main bang, the original ultrasound pulse which is directed towards the eye. Pulse 63 represents the reflected echo pulse from the cornea anterior surface and the pulse 64 is the echo pulse reflected from the cornea posterior surface or endothelium layer. The output of the comparator 60 is converted into pulses having width of 100 nanoseconds by the processor 66 which receives and shapes the pulses properly for further processing. The output of the processor 66 is connected to one input of each of the AND gates 70 and 74.

Meanwhile, the output of the clock 50 is extracted along the line 75 (designed by the lable "TO A") and is connected to the point labeled "A", where it is passed through a 6-microsecond delay 76 corresponding to the nominal time required for the reflected echo pulse from the anterior surface to reach the transducer and a 1-microsecond window 77. The 1-microsecond window allows for dimensional variations of the probe tip.

During the 1-microsecond window, AND gate 70 will have a positive output only when pulse 63 is detected. A pulse not arriving within the proper window is treated by the circuit as a spurious pulse, and is discarded. If the pulse is spurious, the absence of a positive output in AND gate 70 will inhibit further measurement of corneal thickness during this particular cycle of operation.

The output of the AND gate 70 is passed through a 300 nanosecond delay 78 and a 1.5 microsecond window 79, the output of which is ended with the posterior cornea surface echo pulse 64. The AND gate 74 will show a positive output upon detection of the posterior surface.

The output of the AND gate 70 is connected to the SET input of the flip-flop 84 and the output from the AND gate 74 is connected to the RESET side of flip-flop 84. The output of the flip-flop 84 is therefore the gate pulse 86, whose leading edge 87 represents the beginning of the cornea anterior surface echo pulse and whose trailing edge 88 represents the cornea posterior surface echo pulse. The gate pulse 86 corresponds to the gage pulse 18 shown in FIG. 1, but of course, the gate pulse 86 is, in practice, very narrow due to the thinness of the cornea, as described above.

The gate pulse 86 is then directed into the pulse stretcher 90 which increases the width of the gate pulse by a predetermined factor, preferably ten. As illustrated in FIG. 13, the output of pulse stretcher 90 is connected to an input of the AND gate 92. The other input of the AND gate 92 is an 8.1 MHz clock 94 which generates pulses in a manner similar to that of the clock 20 in FIG. 11. Because the pulses produced by the pulse stretcher 90 are ten times wider than they were originally, the clock 94 can operate at the relatively low frequency of 8.1 MHz and retain the desired accuracy and resolution in the readout. The pulses leaving the AND gate 92 are counted in the counter 96, and the output of the counter 96 is displayed in a visual digital display unit 98 in an appropriate manner.

Figure 12:
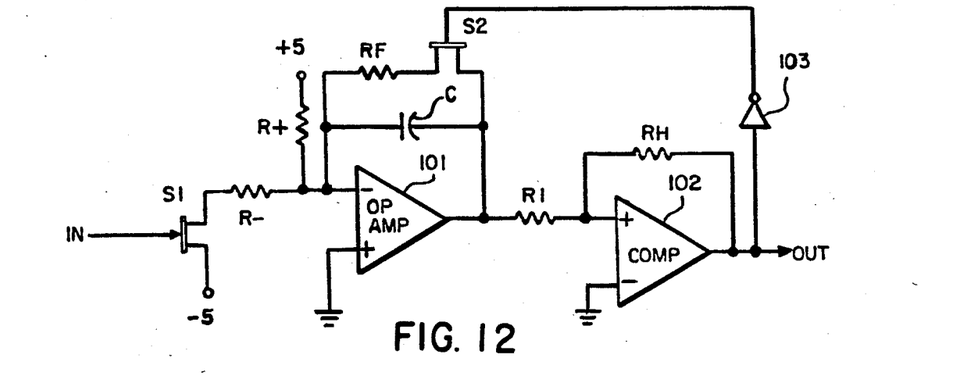
FIG. 12 is a schematic circuit diagram showing the pulse stretcher of the present invention.

The construction details of the pulse stretcher 90 are shown in FIG. 12 in schematic form. The essential part of the operation is controlled by solid state switches S1 and S2. During quiescent conditions, switch S1 is turned off, switch S2 is turned on, and the operational amplifier 101 has an output which settles to a small negative voltage determined by $-(RF/R+)$ 5 volts. The solid state switches can be field effect transistors, but more preferably are a combination of field effect transistors to provide better isolation and sharper switching response. The slightly negative output of the operational amplifier 101 biases the comparator 102 low, which in turn keeps the solid state switch S2 closed by virtue of the invertor 103.

When an input pulse enters the pulse stretcher 90, the switch S1 closes and because $R-$ is smaller than $R+$, the output of the operational amplifier output passes through zero (from its slightly negative equilibrium state), the output of comparator 102 goes high opening switch S2 so that the operational amplifier 101 becomes an integrator, due to the influence of the capacitor C.

When the input pulse ends, the switch S1 opens, so that the input to the operational amplifier 101 (which is now integrating) is driven positive by the voltage applied through $R+$. This positive input causes the integrator output to tend toward zero. Until the integrator becomes slightly negative again, the output of the comparator 102 stays high, maintaining the positive output and keeping the switch S2 open. The operational amplifier 101 (acting as an integrator) eventually goes slightly below zero to overcome the current through the comparator hysteresis resistor RH and the comparator output drops low, ending the positive output.

The output of the pulse stretcher 90 can deviate from the desired output for two reasons; namely, gain error and offset error. This output can be described by the equation $$T_O = KT_I + L$$

where $T_O$ is the output pulse width, $T_I$ is the input pulse width, K is the time multiplication factor (gain) and L is the time offset. Ideally, $K=10$ and $L=0$.

To change, L, RF is changed. The resistor RF sets the equilibrium state and therefore determines how much of the input pulse is spent in overcoming this negative state before the output starts. L will be zero when this effect exactly cancels the termination delay caused by the hysteresis resistor RH.

The value of K is changed by changing $R-$. The resistor $R-$ determines how fast the input pulse is integrated and therefore, the point from which the current through $R+$ must restore zero. This adjustment capability for gain provides the additional feature that the differences in the velocity of sound through different materials can be compensated for by adjusting the gain as compared to the conventional method of changing the counter clock frequency.

Figure 14:
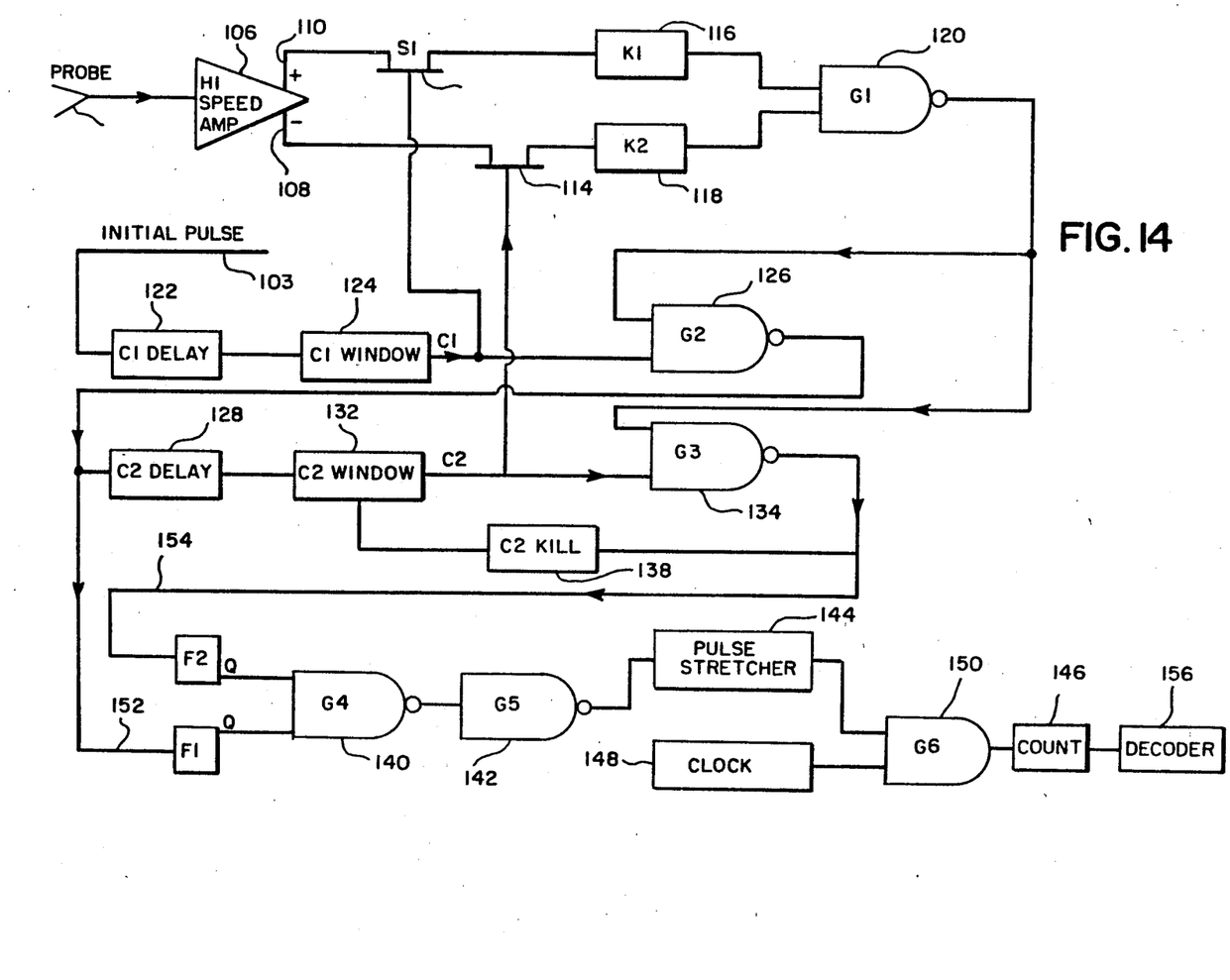
FIG. 14 is a block diagram of the gating circuitry.

Referring now to FIG. 14, a block diagram of the gating circuitry of an ultrasound pachometer suitable for measuring the thickness of an extremely thin member, for example, the thickness of a particular area of the cornea is set forth. A means of generating an ultrasonic initial pulse 103 to be applied to an ultrasonic piezoelectric transducer contained within a hand-held probe 104 is provided in well known manner. In practice, transmission and reception of the ultrasonic pulses results when the tip of the hand-held probe is touched to the anterior surface of the cornea, as illustrated in FIGS. 1 and 10.

The received echoes are directed to a high-speed amplifier 106 which functions to amplify the received echoes and also to clip the initial pulse that is sent to the transducer so that it will not interfere with measurement. The amplifier 106 is to produce both inverted and non-inverted outputs with low phase error. A pair of FET switches 112, 114, are wired in series with the outputs of the amplifier, switch 112 being in series with the non-inverted output of the amplifier 106 and switch 114 being in series with the inverted amplifier output. The FET switches are turned on and off by two "window" signals from the gating circuitry as hereinafter more fully set forth.

The outputs from the FET switches 112, 114, are inputs to two comparators 116, 118, the output from switch 112 being the input to comparator 116 and the output from switch 114 being the imput to comparator 118 respectively. Preferably, provision is made for adjusting the comparators so that they trigger on the second positive swing of their inputs because this wavefront has been determined emperically to be more stable with respect to position and amplitude than the first wavefront. The outputs of the comparators 116, 118 are the inputs of NAND gate 120 so that triggering of either comparator will change NAND gate 120 output to HIGH.

In one particular version of the gating circuitry, a combination of two monostable multivibrators (one-shot) labeled C1 Delay 122 and C1 Window 124 are provided. The C1 Delay 122 is wired to trigger when the ultrasonic pulse 103 is sent. The C1 Window 124 is wired to trigger on the falling edge of the C1 Delay output. This particular combination has been provided to create a time window during which echoes can be received and processed, to the exclusion of other spurious or invalid echoes. The C1 Delay 122 and C1 Window 124 combination in particular processes the echo from the anterior corneal surface 8. The C1 Window 124 is also directed to the FET switch 112.

As illustrated, the output of NAND gate 120 is directed to the input to NAND gate 126 and the output from C1 Window 124 is the other input whereby the output of NAND gate 126 will be LOW when the NAND gate 120 output is HIGH (indicating the presence of an accepted echo) and output of C1 Window 124 is HIGH (indicating the presence of a window for reception of the echo from the anterior corneal surface 8. The output of NAND gate 124 is utilized as the trigger for the one-shot C2 Delay 128 and additionally as the clock input for the flip-flop 130. The flip-flop 130 is provided to start the signal which is to be sent to the pulse stretcher 144.

The output of the C2 Delay 128 is arranged to trigger on the falling edge of the signal from NAND gate 126 and is employed as the trigger for one-shot C-2 Window 132. Additionally, the C2 Delay output is employed as the RESET for the C1 Window 124 in known manner whereby C1 Window 124 is set LOW when C2 Delay 128 opens.

The output of C2 Window 132 is an input to NAND gate 134. The other input is the NAND gate 120 output as shown. The output of NAND gate 134 will be LOW when C2 Window 132 is HIGH and the NAND gate 120 output is HIGH. In this manner, an echo from the posterior corneal surface 10 can be isolated in time in a manner similar to the way that NAND gate 126 isolates an echo from the anterior corneal surface 8. The C2 Window 132 output is also directed to the FET switch 114.

Still referring to FIG. 14, the output of NAND gate 134 is connected as the clock input to the flip-flop 135, which then functions to end the signal sent to the pulse stretcher 144. The same output also is used as the trigger to the one-shot C2 Kill 138. The output of the one-shot C2 Kill 138 is activated to trigger on the falling edge of the output from NAND gate 134 and is connected as input to the RESET of one-shot C2 window 132. Whereby, after function of C2 Kill has begun, the C2 Window 132 will be reset to LOW and will remain that way.

The flip-flop 130 is set at the beginning of each pulse transmission to output a LOW from the Q output, but will output a HIGH as soon as the clock 152 goes LOW, due to the settings of the J and K inputs. The flip-Flop 136 is set at the beginning of plate pulse transmission to output a HIGH from the Q-NOT output, but will output a LOW as soon as the clock 154 goes LOW, due to the settings of the J AND K inputs. This will be the same as flip-flop 130, except that a different output is used.

NAND gate 140 has its inputs Q from flip-flop 130 and Q-NOT from the flip-flop 136 so that it will initially output a HIGH. That HIGH will become a LOW when the first echo is received and flip-flop 130 outputs a HIGH, and that LOW will become a HIGH again when the second echo is received and flip-flop 136 outputs a LOW. NAND gate 142 is in series with the output of NAND gate 140 and functions as an inverter. The output of NAND gate 142 is the input of the pulse stretcher 144.

The pulse stretcher 144 and clock 148 outputs are the inputs of the AND gate 150. During the time that the pulse stretcher 144 is not putting out pulses, the output of AND gate 150 will be LOW. A counter 146 measures the duration of the stretched pulse from the pulse stretcher 144 by using the clock 148 which has a precise frequency and by counting the number of clock cycles during the pulse. When the counter 146 is not operative, the pulse will go to HIGH and the clock 148 will then cause the output of AND gate 150 to toggle between 0 and 1. When the pulse stretcher 144 output goes to LOW, then AND gate 150 will be locked whereby a precise number of pulses can be counted by the counter 146.

The preferred embodiment of the gating circuitry can be designed in known manner to include a decoder 156 to convert the number of cycles counted by the counter 146 to a digital display, which would then be a digital display of the thickness of the cornea. Additional accessories such as a foot operated switch (not shown) can be included to initiate the initial pulse 103, thereby freeing the operator's hands for other duties. Other features, such as visible display of the amplitude of the echoes being received, and circuitry means to detect errors such as overflow of the counters or range errors in instrument settings together with means to display them could also be added in known manner by those skilled in the art.

It is understood that the above description of the preferred embodiment is only illustrative of the manner in which the present invention can be practice. Other variations are possible, for example, the pulses could be electromagnetic and not ultrasonic. The precise manner in which the probe and blade assembly is constructed can be varied. The mechanism for advancing the blade may use electromagnetic, hydraulic, or pneumatic force. It is understood that these and other variants are included within the scope of the claims appended hereto.

What is claimed is:

1. In an apparatus for performing corneal surgery by measuring local cornea thickness by employing a handheld probe, the measurement of thickness being made by positioning the probe normal to surface of the cornea to produce first and second reflected ultrasonic pulses respectively from the anterior surface and the posterior surface of the cornea, and then measuring the time interval between the first and second pulses, the improvement which comprises means for generating a gate pulse having a duration substantially equal to the time interval between said reflected first and second pulses;

means for stretching said gate pulse by a predetermined factor, said factor being at least about ten; and means for measuring the duration of the gate pulse and for converting said measurement into an electronic signal.

2. The apparatus of claim 1 comprising means to disregard extraneous pulses other than the said first and second pulses in the event that such extraneous pulses are generated by local conditions present at the interface between the probe and the cornea the means to disregard further comprising gating circuitry providing timed windows within which time only the first and second pulses can be received.

3. A method of aiding corneal surgery comprising applying a probe normal to the surface of the cornea and directing a pulse of energy towards the cornea, creating a first reflected pulse from the anterior cornea surface and a second reflected pulse from the posterior cornea surface;

measuring the time interval between the first and second pulses, the measuring comprising generating a gate pulse having a duration substantially equal to the time interval between the first and second pulses and stretching the gate pulse by a predetermined factor; and converting the measured time interval into an equivalent measured distance, the measured distance being the thickness of the cornea at the location of the application of the probe.

4. The method of claim 3 and the additional step of contacting the cornea with the probe to direct the pulse of energy.

5. A method determining corneal thickness by measurement of the time interval between a first echo pulse reflected from the anterior cornea surface and a second echo pulse reflected from the posterior cornea surface by employing a probe comprising a tip which comprises positioning the tip of the probe adjacent to the cornea to direct a ultrasonic beam toward the cornea and producing a plurality of reflected echo pulses from the cornea;

directing a zeroing echo pulse reflected from the interface between the cornea and the probe tip to allow an acoustically cleaner signal from the cornea;

aiming an electronic gate to expect a first echo pulse from the anterior cornea surface within a predetermined span of time after the zero echo pulse, said predetermined time span being chosen to select pulses reflected only from the anterior cornea surface;

detecting the first echo pulse reflected from the anterior cornea surface;

activating a measurement apparatus in response to the arrival of the first echo pulse within the predetermined time span;

detecting the second echo pulse reflected from the posterior cornea surface;

deactivating the measurement apparatus when the second echo pulse is detected;

generating a gate pulse having a duration substantially equal to the time interval between the first and second echo pulses; and stretching the gate pulse by a predetermined factor and converting the stretched gate pulse into an equivalent measured distance, the measured distance being the thickness of the cornea at the location of the probe.

6. The method of claim 5 wherein the activating step includes the step of inhibiting the measurement of the time interval between the first and second pulses when the interval between the zero pulse and the first pulse is not within the predetermined span.

* * * * *